(12) United States Patent
Schwab

(10) Patent No.: US 8,529,438 B2
(45) Date of Patent: Sep. 10, 2013

(54) ENDOSCOPIC INSTRUMENT

(75) Inventor: Daniel Schwab, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 240 days.

(21) Appl. No.: 13/074,165

(22) Filed: Mar. 29, 2011

(65) Prior Publication Data
US 2011/0245601 A1 Oct. 6, 2011

(30) Foreign Application Priority Data
Apr. 3, 2010 (DE) .......................... 10 2010 013 803

(51) Int. Cl.
A61B 1/00 (2006.01)

(52) U.S. Cl.
USPC ........... 600/146; 600/147; 600/148; 600/149; 600/150

(58) Field of Classification Search
USPC ................................................ 600/146–152
See application file for complete search history.

(56) References Cited

U.S. PATENT DOCUMENTS

| | | | | |
|---|---|---|---|---|
| 3,897,775 A | * | 8/1975 | Furihata | 600/131 |
| 4,108,011 A | * | 8/1978 | Gregg et al. | 474/153 |
| 4,557,254 A | * | 12/1985 | Yamaguchi | 600/149 |
| 4,559,928 A | | 12/1985 | Takayama | |
| 4,688,555 A | * | 8/1987 | Wardle | 600/149 |
| 4,718,407 A | * | 1/1988 | Chikama | 600/150 |
| 4,941,455 A | * | 7/1990 | Watanabe et al. | 600/146 |
| 5,388,568 A | * | 2/1995 | van der Heide | 600/146 |
| 5,667,476 A | * | 9/1997 | Frassica et al. | 600/149 |
| 6,236,876 B1 | | 5/2001 | Gruner et al. | |
| 6,440,062 B1 | * | 8/2002 | Ouchi | 600/146 |
| 6,709,667 B1 | * | 3/2004 | Lowe et al. | 424/422 |
| 6,793,622 B2 | * | 9/2004 | Konomura et al. | 600/152 |
| 2004/0193016 A1 | * | 9/2004 | Root et al. | 600/146 |

FOREIGN PATENT DOCUMENTS

| | | |
|---|---|---|
| JP | 02-102632 A | 4/1990 |
| JP | 11-113838 A | 4/1999 |
| WO | 9200696 A1 | 1/1992 |

OTHER PUBLICATIONS

Office Action issued on Oct. 5, 2010 in DE Application No. 10 2010 013 803.7-51.
Office Action issued Jul. 7, 2011 in GB Application No. 1104949.1.

* cited by examiner

*Primary Examiner* — Matthew J Kasztejna
(74) *Attorney, Agent, or Firm* — Panitch Schwarze Belisario & Nadel LLP

(57) ABSTRACT

An endoscopic instrument includes an instrument section which may be deflected transversely to the instrument axis. The instrument section is connected via at least one control wire to an actuation element arranged on the instrument at the proximal side. A safety coupling, which limit a force exerted by the actuation element onto the control wire, are arranged between the control wire and the actuation element.

9 Claims, 2 Drawing Sheets

ENDOSCOPIC INSTRUMENT

BACKGROUND OF THE INVENTION

The present invention relates generally to an endoscopic instrument with a deflectable distal instrument section.

The starting point of the present invention are those endoscopic instruments, with which a distal end section may be deflected transversely to the instrument longitudinal axis. The exact deflection of this section is controlled by way of Bowden cables. These Bowden cables are coupled in movement to rotatable control wheels which are arranged on the handles of these instruments. The deflection of the distal end sections, with these instruments, is effected by way of rotating the control wheels and a tensile loading of the Bowden cables caused by this.

It has been found that an incorrect operation of the control wheels, i.e. a too forceful rotation of the control wheels, as the case may be, may lead to a Bowden cable coupled thereto, itself tearing or this tearing in the region of its fastening on the distal end section to be deflected, which causes immediate failure of the instrument and renders necessary comparatively complicated and accordingly expensive repair work.

A medical instrument is known from U.S. Pat. No. 6,236,876 B1, with which a distal end section may be deflected by way of Bowden cables which in each case are coupled to an electric drive motor. The drive shafts of the motors are in each case coupled to a rotatably mounted disk, on which two Bowden cables are fastened, via a friction wheel as a slip-coupling, in order to prevent too large tensile forces acting on the Bowden cables.

An endoscope with a distal end section which may be deflected via guide wires and with which the guide wires are arranged within the spiral springs for overload protection, is described in JP 11-113838 A.

BRIEF SUMMARY OF THE INVENTION

Against this background, it is an objective of the present invention to provide an endoscopic instrument, which has a greater operational reliability and a reduced repair need, compared to known instruments of this type.

The above objective is achieved by an endoscopic instrument as shown and described herein. Advantageous further formations of this instrument are to be deduced from the dependent claims, the subsequent description as well as the drawing. Hereby, according to a preferred embodiment of the present invention, the features which are specified in the dependent claims and in the description, in each case on their own or also in a suitable combination, may further form the solution according to the invention and according to the independent claim(s).

The endoscopic instrument according to a preferred embodiment of the present invention comprises a deflectable instrument section. The deflection direction of this instrument section is basically infinite. Preferably, the instrument section is deflectable at least transversely or obliquely to the instrument axis. For this, the instrument section is connected via at least one control wire or Bowden cable to an actuation element arranged on the instrument at the proximal side. Usually, also two control wires may engage on two sides of the instrument section which are distanced diametrically from one another, on the deflectable instrument section, wherein these two control wires in each case are connected in movement to the actuation element. This design permits the instrument section to be deflected in a first direction by way of tensile loading of a first control wire and into a direction opposite to this or back, by way of a tensile loading of the other control wire. Moreover, the deflectable instrument section may also be deflectable in two planes which are normal to one another. In this case, a first control wire pair which is connected to the first actuation element, may be provided for the deflection of the instrument section in a first plane, while a second control wire pair which is connected a second actuation element, is provided for the deflection of the instrument section in a plane which is normal to the first plane.

According to a preferred embodiment of the present invention, a safety coupling as force limitation means which limits a force exerted by the actuation element onto the control wire, is arranged between the at least one control wire and the actuation element. The safety coupling interrupts the force transmission from the actuation element to the control wire, without destruction, i.e. in a reversible manner, before a force which is transmitted via the actuation element onto the control wire, reaches a critic value which leads to a tearing of the control wire at the instrument section to be deflected or to a tearing of the control wire per se. In as much as this is concerned, an incorrect forceful actuation of the actuation element with the instrument according to the invention does not lead to a damage of the instrument, in contrast to the instruments of this type which have been known until now.

The instrument according to a preferred embodiment of the present invention is preferably a medical or technical flexible endoscope which comprises a shank which is to be introduced into a body opening, cavity or likewise. With regard to this instrument, the actuation element and the safety coupling are advantageously arranged on or in a handle which is provided on the proximal side of the shank. The actuation element is arranged on the outer side of the handle, whilst the safety coupling is preferably arranged within the handle, for actuating a shank section which is controllable at the distal side.

In a further formation of this design, the control wire may advantageously be fastened on a fastening element which is rotatably mounted in the handle and which is coupled in movement, via the safety coupling, to the actuation element which is likewise rotatably mounted in the handle. With regard to the fastening element, it may be the case for example of a rotary disk, on which the at least one control wire or a control wire pair is fastened in the region of the outer periphery, in a manner corresponding to the fastening position of the control wire or the control wires on the deflectable instrument section. The rotatably mounted actuation element may be designed as a lever or as an actuation wheel, which is ergonomically more favorable.

Via the safety coupling, a torque exerted manually on the actuation element is transmitted onto the fastening element, by which means the at least one control wire is loaded in tension. The safety coupling is typically designed in a manner such that it interrupts the torque transmission from the actuation element to the fastening element on reaching a defined torque, which when exceeded would lead to a critical tensile loading of the control wire.

With the endoscopic instrument according to the present invention, the rotation axis of the fastening element is distanced to the rotation axis of the actuation element is however preferable. Accordingly, the rotation axis of the fastening element and the rotation axis of the actuation element are preferably arranged at a distance next to one another in the direction of the longitudinal extension of the handle.

A belt drive forms the safely coupling. Accordingly, the rotatably mounted actuation element as well as the rotatably mounted fastening element may be coupled in each case to a belt pulley, wherein the two belt pulleys are connected in a rotationally movable manner by way of a belt. Basically, any belt types such as e.g. flat belts or V-belts may be used in this context.

Particularly advantageously, the belt drive is however designed as a toothed belt drive. Usefully, one uses those toothed belts which have such a large elasticity that the toothed pairing between the toothed belt and a toothed wheel of the toothed belt drive which may be coupled in movement to the actuation element or to the fastening element, in the case of an overload, may be released by way of deformation of the toothed belt and/or its teeth, so that the toothed belt drive may fulfill its function as a safety coupling. For this, the applied toothed belt may for example be designed of a plastic material or rubber material of a suitable elasticity. This elasticity is typically selected in a manner such that the toothed belt permits a positive-fit movement coupling of the actuation element to the fastening element, below a critic load.

Further advantageously, the toothed wheel which is rotatably connected to the actuation element and the toothed wheel which is rotatably connected to the fastening element may in each case be surrounded by a guide for the toothed belt, in a peripheral section. Accordingly, with this further design, a guide body may be provided on the outer side of the periphery of these toothed wheels and this guide body is designed in a bent manner preferably in a ring-segment-shaped or U-shaped manner. A suitably large play is formed between the toothed wheels and the side of the guide which faces the toothed wheels, in order to permit an unhindered movement of the toothed belt spanned out on these toothed wheels.

Hereby, the guide however is preferably radially distanced to one of the toothed wheels in a manner such that the toothed belt of the toothed belt drive may not disengage at this toothed wheel. For example, the radial distance between the toothed wheel and the guide is preferably selected smaller than the height of the tooth of the toothed belt or of the toothed wheel.

Usefully, one of the guides for forming a safely coupling and which surrounds the toothed wheels, is distanced radially to one of the toothed wheels, such that the toothed belt on this toothed wheel may disengage on exceeding a certain force, so that the movement coupling of the actuation element to the fastening element in this case is released until the acting force again has a value which lies below a critic value. The distance between the toothed wheel and the guide which surrounds this toothed wheel is thus selected preferably of such a magnitude, that the intermediate space between the toothed wheel and the guide may completely accommodate the toothed belt which is not engaged with the toothed wheel, and prevents a slipping-away to the side.

BRIEF DESCRIPTION OF THE SEVERAL VIEWS OF THE DRAWINGS

The foregoing summary, as well as the following detailed description of a preferred embodiment of the present invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
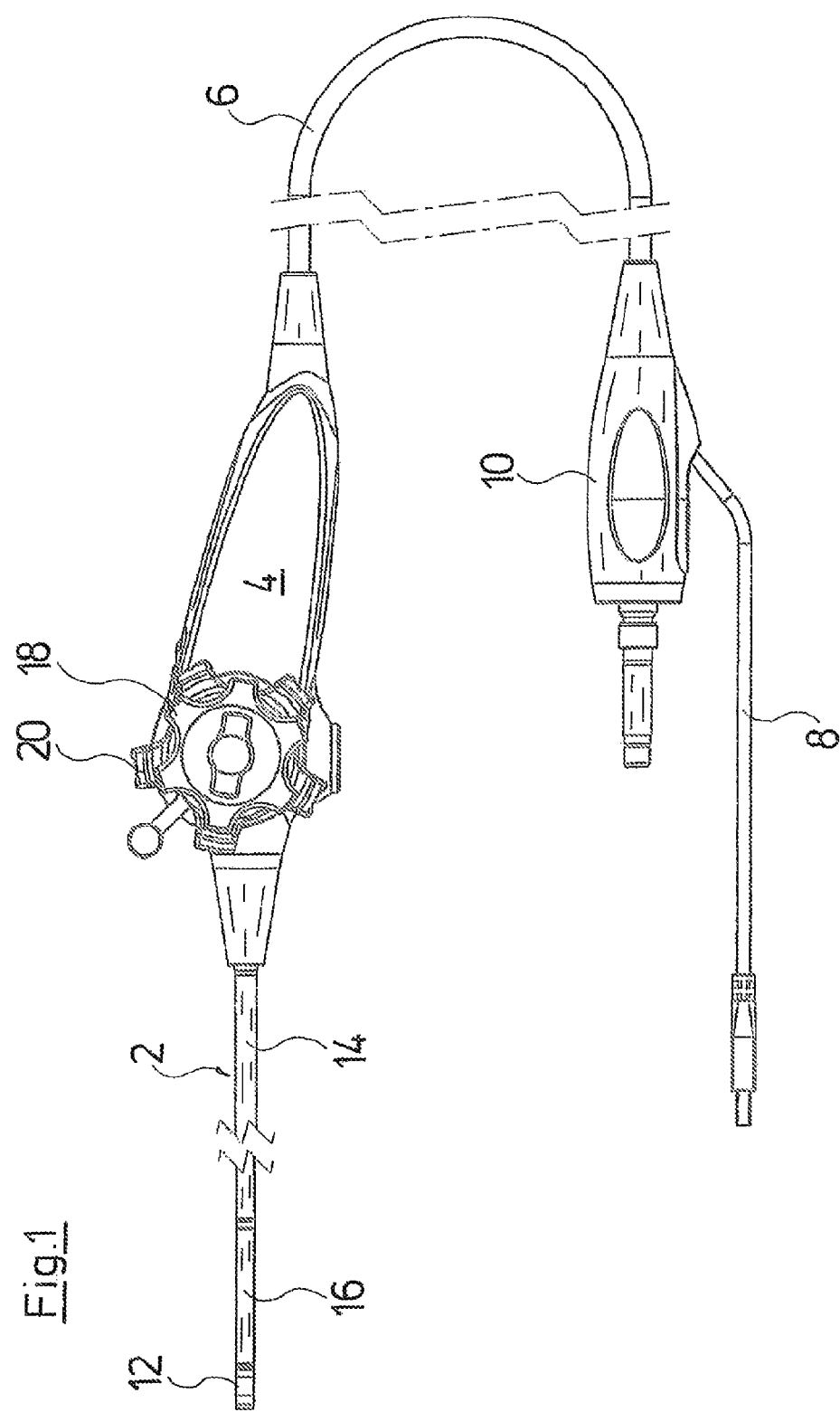
FIG. 1 is schematic side view of an endoscopic instrument with a deflectable instrument section in accordance with a preferred embodiment of the present invention.

Certain terminology is used in the following description for convenience only and is not limiting. The words "proximal" and "distal" designate directions in the drawings to which reference is made. Unless specifically set forth herein, the terms "a," "an" and "the" are not limited to one element, but instead should be read as meaning "at least one." The terminology includes the words noted above, derivatives thereof and words of similar import.

With regard to the endoscopic instrument represented in FIG. 1, it is the case of a flexible medical instrument or technical endoscope with a shank 2 which may be introduced into a body opening. The shank 2 which is designed as a hollow shank, connects onto a handle 4 at the distal side, and this handle 4 forms a grip part with the essential operating elements of the instrument. A flexible tube 6 is fastened on the handle 4 at the proximal side of the handle 4. This flexible tube 6 serves for receiving a fiber-optic cable and electrical connections from the housing part 10 to an instrument head 12 which is arranged at the distal end of the shank 2 and having the optical and electronic components arranged therein.

The shank 2 has a flexible shank section 14 which connects directly to the handle 4. A section 16 of the shank 2 which is deflectable in two planes which are aligned normally to one another, transversely and obliquely to the longitudinal extension of the section 14, connects on the distal side of the section 14.

Two control wire pairs which are led through the shank 2 and which are fastened in the region of the distal end of the shank 2 are provided for the deflection of the section 16. For actuating the control wire pairs, two actuation elements 18 and 20 in the form of star wheels are arranged on the handle 4 and are coupled in movement in each case to a control wire pair, which is described in detail hereinafter in combination with FIG. 2 by way of the actuation element 18.

Figure 2:
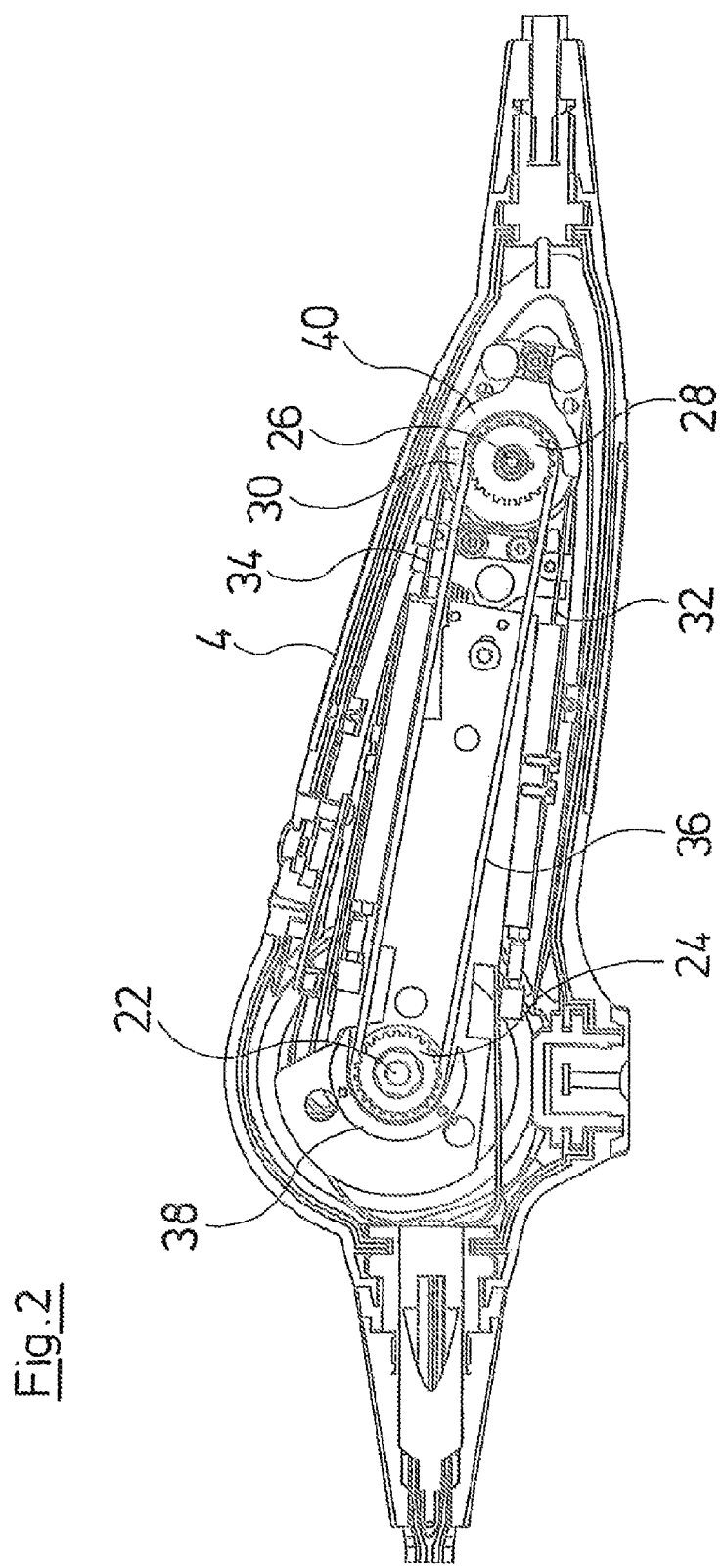
FIG. 2 is a longitudinal section view of a handle of the instrument according to FIG. 1.

The actuation element 18 which is not evident in FIG. 2 is fastened on a shaft 22 which is rotatably mounted in the handle 4. A toothed wheel 24 is also rotatably movably connected to the shaft 22. A further shaft 26 is rotatably mounted in the handle 4, in a parallel alignment to the shaft 22 and distanced to the shaft 22 in the proximal direction. A toothed wheel 28 as well as a rotary disk 30 is likewise fastened on this shaft 26. The rotary disk 30 forms a fastening element 30 for a control wire pair consisting of the control wires 32 and 34 which are fastened lying diametrically opposite one another on the outer periphery of the rotary disk 30, and at the distal end of the handle 4 are led out of this into the shank 2.

For actuating the control wires 32 and 34, the toothed wheels 24 and 28 together with a toothed belt 36 spanned thereover, form a toothed belt drive, via which the rotary disk 30 with the control wires 32 and 34 coupled thereon, is coupled in movement to the actuation element 18. This toothed belt drive permits a transmission of the rotation movement of the actuation element 18 onto the rotary disk 30, by which means a tensile force which effects a suitable deflection of the section 16 of the shank 2, is exerted either onto the control wire 32 or onto the control wire 34, depending on the rotation direction of the actuation element 18.

The toothed wheel 24 at its outer side which is away from the toothed wheel 28 is surrounded by a U-shaped guide 38. The distance between the guide 38 and the toothed belt 36 located thereunder is selected such that the toothed belt 36 may not laterally jump from the toothed wheel 24. A guide 40 which surrounds the toothed belt spanned on the toothed wheel 28, on the outer side in a ring-segment-shaped manner, is also arranged on the outer side of the toothed wheel 28 which is away from the toothed wheel 24.

The toothed belt drive is designed as a safety coupling, in order to prevent a too forceful operation of the actuation element 18 leading to a tearing away or tearing of the control wires 32 and 34 which are coupled in movement thereto. For this, the toothed belt 36 has such an elasticity which, given a too forceful operation of the actuation element 18, leads to the toothed belt 36 being able to disengage at a suitable location of the toothed belt drive. This disengagement may be effected at the toothed wheel 28 with the represented embodiment example. For this purpose, a guide surface of the guide 40 which faces the outer periphery of the toothed belt 36, is distanced from the outer side of the toothed belt 36 which is away from the toothed wheel 28, in the radial direction of the toothed belt 36, to such an extent that the intermediate space which is thus formed between the toothed belt 36 and the guide 40 may essentially completely accommodate the toothed belt which is disengaged. With a wear of the toothed belt 36 which is caused by a frequent incorrect operation of the actuation element 18, this may be easily exchanged in the handle 4.

Finally, it should be noted that although it is not evident in the drawing, the actuation element 20, analogously to the actuation element 18, in the handle 4, is coupled in movement via a second belt drive to a further fastening element and to a second control wire pair fastened thereon.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An endoscopic instrument comprising a deflectable distal instrument section connected via at least one control wire (32, 34) to an actuation element (18) arranged on the endoscopic instrument at a proximal side thereof, wherein a safety coupling, which limits a force exerted by the actuation element (18) onto the control wire (32, 34), is arranged between the control wire (32, 34) and the actuation element (18), and wherein a toothed belt of a belt drive forms the safety coupling, the toothed belt having elasticity which relieves an overload by deformation of the toothed belt or teeth thereof.

2. The endoscopic instrument according to claim 1, wherein the actuation element (18) and the safety coupling are arranged on or in a handle (4) provided on a proximal side of a shank (2).

3. The endoscopic instrument according to claim 2, wherein the at least one control wire (32, 34) is fastened on a fastening element (30) which is rotatably mounted in the handle (4) and which via the safety coupling is coupled in movement to the actuation element (18) which is likewise rotatably mounted in the handle (4).

4. The endoscopic instrument according to claim 3, wherein a rotation axis of the fastening element (30) is distanced to a rotation axis of the actuation element (18).

5. The endoscopic instrument according to claim 1, further comprising a first toothed wheel (24) rotationally movably connected to the actuation element (18) and surrounded in a peripheral section by a first guide (38).

6. The endoscopic instrument according to claim 5, further comprising: a second toothed wheel (28) rotationally movably connected to a fastening element (30) and surrounded in a peripheral section by a second guide (40).

7. The endoscopic instrument according to claim 6, wherein the first guide (38) is distanced radially from one of the toothed wheels (24, 38) in a manner such that the toothed belt (36) may not disengage at the one of the toothed wheels (24, 28).

8. The endoscopic instrument according to claim 6, wherein the second guide (40) is distanced radially from one of the toothed wheels (24, 28) in a manner such that the toothed belt (36) may disengage the second toothed wheel (28) on exceeding a predetermined force.

9. An endoscopic instrument comprising:
a deflectable distal instrument section connected via at least one control wire (32, 34) to an actuation element (18) arranged on the instrument at a proximal side thereof; and
a safety coupling arranged between the at least one control wire (32, 34) and the actuation element (18), the safety coupling limiting a force exerted by the actuation element (18) onto the control wire (32, 34),
wherein a belt drive forms the safety coupling,
wherein the actuation element (18) and the safety coupling are arranged on or in a handle (4) provided on a proximal side of a shank (2), and
wherein the control wire (32, 34) is fastened on a fastening element (30) which is rotatably mounted in the handle (4) and which via the safety coupling is coupled in movement to the actuation element (18) which is likewise rotatably mounted in the handle (4), the fastening element (30) being a rotary disc.

* * * * *